United States Patent [19]

Figuerido

[11] Patent Number: 5,643,235

[45] Date of Patent: Jul. 1, 1997

[54] TUBULAR DEVICE FOR THE PENIS OF AN INCONTINENT MALE

[76] Inventor: Kim A. Figuerido, 33 Leo Ave., Providence, R.I. 02904

[21] Appl. No.: 552,716

[22] Filed: Nov. 3, 1995

[51] Int. Cl.[6] .................................................. A61F 5/44
[52] U.S. Cl. ...................... 604/352; 604/349; 604/385.1
[58] Field of Search ................................. 604/349, 351, 604/352, 385.1, 367; 128/84.4

[56] References Cited

U.S. PATENT DOCUMENTS

| | | | |
|---|---|---|---|
| 4,576,599 | 3/1986 | Lipner | 604/352 |
| 4,863,448 | 9/1989 | Berg | 604/352 |
| 5,382,245 | 1/1995 | Thompson et al. | 604/367 |

*Primary Examiner*—Robert A. Clarke

[57] ABSTRACT

A tubular device for the penis of an incontinent male including a tube. The tube has a closed hemispherical distal end and an open generally circular proximal end. The tube has a central axis when in use with a cylindrical wall of a diameter increasing from the distal end to the proximal end. Included is a pair of axle slits extending from the proximal end. The slits thereby divide the proximal end into a major circumferential extent and a minor circumferential extent. A pair of circumferential tabs are provided. The tabs extend from the major circumferential extent from adjacent to each slit to overlie the minor circumferential extent of the tube thereadjacent. Lastly, an adhesive is included. The adhesive is on the radially interior face of each tab for contacting the minor circumferential extent to allow the proximal end of the tube to be securely positioned at the base of the penis.

1 Claim, 2 Drawing Sheets

TUBULAR DEVICE FOR THE PENIS OF AN INCONTINENT MALE

BACKGROUND OF THE INVENTION

1. Field of the Invention

The present invention relates to a tubular device for the penis of an incontinent male and more particularly pertains to a device with hydrophobic and hydrophilic layers positionable over the penis of an incontinent male.

2. Description of the Prior Art

The use of devices for incontinent males is known in the prior art. More specifically, such devices heretofore devised and utilized for the purpose of absorbing dribbling are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 5,074,853 to Bryant discloses a male incontinence diaper. U.S. Pat. No. 5,009,649 to Goulter et al discloses an expandable banded male urinary incontinence condom and supporting undergarment. U.S. Pat. No. 4,790,835 to Elias discloses a urinary male diaper. U.S. Pat. No. 4,673,401 to Jensen and Ferguson discloses a male incontinence device. U.S. Pat. No. 4,944,733 to Casaie discloses a diaper for use in toilet training male children or for use by incontinent male adults. Lastly, U.S. Pat. No. 4,675,012 to Rooyakkers discloses a method of forming an absorbent genitalia pouch for incontinent males.

While these devices fulfill their respective, particular objectives and requirements, the aforementioned patents do not describe tubular device for the penis of an incontinent male that allows a comfortable device having a hydrophobic and hydrophilic inner layer that fits over the penis for moisture absorption and is small enough to fit under a pair of trousers.

In this respect, the tubular device for the penis of an incontinent male according to the present invention substantially departs from the conventional concepts and designs of the prior art, and in doing so provides an apparatus primarily developed for the purpose of a device with hydrophobic and hydrophilic layers positionable over the penis of an incontinent male.

Therefore, it can be appreciated that there exists a continuing need for a new and improved tubular device for the penis of an incontinent male which can be used as a device with hydrophobic and hydrophilic layers positionable over the penis of an incontinent male. In this regard, the present invention substantially fulfills this need.

SUMMARY OF THE INVENTION

In view of the foregoing disadvantages inherent in the known types of devices for incontinent males now present in the prior art, the present invention provides an improved tubular device for the penis of an incontinent male. As such, the general purpose of the present invention, which will be described subsequently in greater detail, is to provide a new and improved tubular device for the penis of an incontinent male and method which has all the advantages of the prior art and none of the disadvantages.

To attain this, the present invention essentially comprises a tube. The tube has a closed hemispherical distal end and an open generally circular proximal end. The tube has a length that is between about 6 to 7½ inches. The tube has a central axis when in use with an imperforate cylindrical wall of a diameter from about 2 inches to 2½ inches and increasing evenly from the distal end to the proximal end. The hemispherical distal end and the cylindrical wall constituting about seventy-five percent of the length of the tube. Included is a pair of axle slits. The slits extend from the proximal end. The slits have a length of about from ⅓ inch to ¼ inch form the proximal end for a distance of about twenty five percent of the length of the tube. The slits divide the proximal end into a major circumferential extent and a minor circumferential extent that extends axially form the distal end at an equal distance. Also, provided is a pair of lateral tabs. The tabs extend from the major circumferential extent from adjacent to each slit to over lie different regions of the minor circumferential extent of the tube thereadjacent. Each tab has a width of about ½ inch and a length being 1 inch form the major circumferential extent. Each tube and the tab is integrally formed of a soft thin flexible rubber. An adhesive is provided on the radially interior face of each tab for contacting the minor circumferential extent. The adhesive allows the proximal end of the tube to be securely positioned at the base of the penis. The adhesive has a layer of protective covering thereon. The protective covering is pulled back and off the adhesive prior to positioning of each tab on to the minor circumferential extent. Each tab is spaced apart from another tab when the adhesive causes each tab to be secured at the base. The adhesive allows the tabs, when posited at the base, to constrict the diameter of the proximal end about 30 to 50 percent. A layer of liquid absorbing hydrophillic material is provided. The hydrophilic material is secured to the entire interior of the tube. Lastly, a layer of dry weave hydrophobic material is secured throughout the layer of hydrophilic material over its entire extent. The hydrophobic material is positioned to be in contact with the penis of a wearer.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved tubular device for the penis of an incontinent male which has all of the advantages of the prior art devices for incontinent males and none of the disadvantages.

It is another object of the present invention to provide a new and improved tubular device for the penis of an incontinent male which may be easily and efficiently manufactured and marketed.

It is further object of the present invention to provide a new and improved tubular device for the penis of an incontinent male which is of durable and reliable constructions.

An even further object of the present invention is to provide a new and improved tubular device for the penis of an incontinent male which is susceptible of a low cost of manufacture with regard to both materials and labor, and which accordingly is then susceptible of low prices of sale to the consuming public, thereby making such tubular device for the penis of an incontinent male economically available to the buying public.

Still yet another object of the present invention is to provide a new and improved tubular device for the penis of an incontinent male which provides in the apparatuses and methods of the prior art some of the advantages thereof, while simultaneously overcoming some of the disadvantages normally associated therewith.

Even still another object of the present invention is to provide a tubular device for the penis of an incontinent male for that has a hydrophobic and hydrophilic layers positionable over the penis of an incontinent male.

Lastly, it is an object of the present invention to provide a new and improved tubular device for the penis of an incontinent male including a tube. The tube has a closed hemispherical distal end and an open generally circular proximal end. The tube has a central axis when in use with a cylindrical wall of a diameter increasing from the distal end to the proximal end. Also included is a pair of axle slits. The slits extend from the proximal end, thereby dividing the proximal end into a major circumferential extent and a minor circumferential extent. A pair of circumferential tabs are provided. The tabs extend from the major circumferential extent from adjacent to each slit to overlie the minor circumferential extent of the tube thereadjacent. Lastly, an adhesive is provided. The adhesive is on the radially interior face of each tab for contacting the minor circumferential extent to allow the proximal end of the tube to be securely positioned at the base of the penis.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts through the various Figures.

DESCRIPTION OF THE PREFERRED EMBODIMENT

Figure 1:
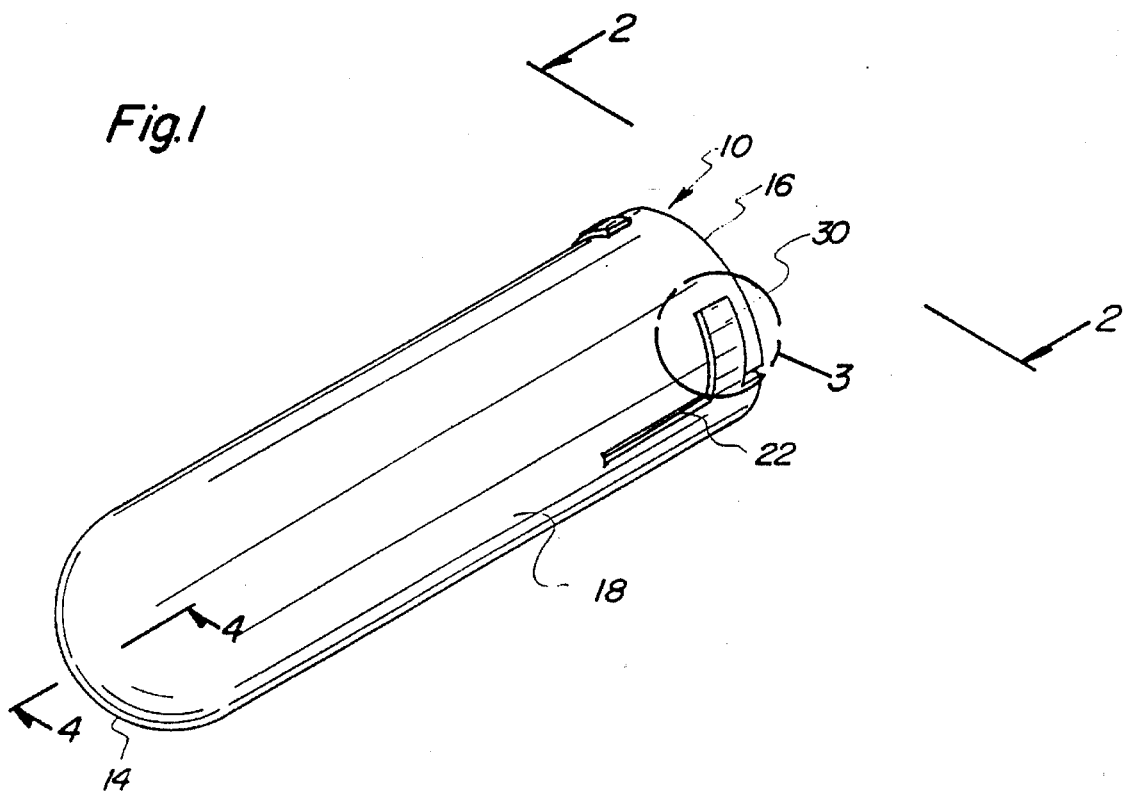
FIG. 1 is a perspective view of the preferred embodiment of the tubular device for the penis of an incontinent male constructed in accordance with the principles of the present invention.

With reference now to the drawings, and in particular to FIG. 1 thereof, the preferred embodiment of the new and improved tubular device for the penis of an incontinent male embodying the principles and concepts of the present invention and generally designated by the reference numeral 10 will be described.

The present invention, the tubular device for the penis of an incontinent male 10 is comprised of a plurality of components. Such components in their broadest context include a tube, a pair of tabs, and an adhesive. Such components are individually configured and correlated with respect to each other so as to attain the desired objective.

Specifically, the present invention includes a tube 12, as shown in FIG. 1. The tube has a closed hemispherical distal end 14 and an open generally circular proximal end 16. The tube has a length that is between about 6 to 7½ inches. This length is designed to accommodate the penis length of a majority of males. The tube has a central axis when in use with an imperforate cylindrical wall 18 of a diameter from about 2 inches to 2½ inches, and increasing evenly from the distal end to the proximal end. The length and width of the device may be increased to accommodate a penis having an greater length and width. The hemispherical distal end and the cylindrical wall constituting about seventy-five percent of the length of the tube. The tube may be slid over the penis of the incontinent male.

Also included is a pair of axle slits 22. The slits extend from the proximal end. The slits have a length of about from ⅓ inch to ¼ inch from the proximal end for a distance of about twenty five percent of the length of the tube. The length of the slits aid in the comfort and fit of the tube around the base of the penis. The slits divide the proximal end into a major circumferential extent 24 and a minor circumferential extent 26. The major circumferential extent and the minor circumferential extent extend axially from the distal end at an equal distance.

Figure 2:
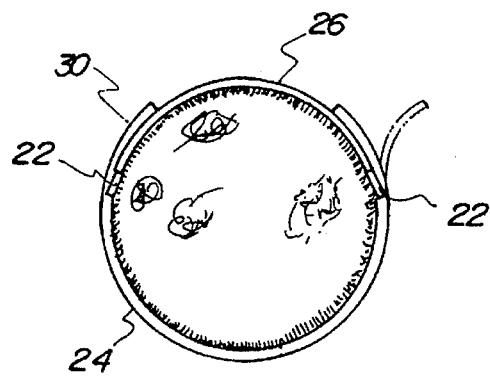
FIG. 2 is an end view of the present invention of FIG. 1 taken along line 2—2 of FIG. 1.

As best illustrated in FIG. 2, a pair of lateral tabs 30 are included. The tabs extend from the major circumferential extent 24 from adjacent to each slit 22 to over lie different regions of the minor circumferential extent 26 of the tube thereadjacent. Each tab has a width of about ½ inch and a length being 1 inch form the major circumferential extent. The length and width of each tab ensures that the tube is positioned snug around the penis. Each tab and the tube are integrally formed of a soft thin flexible rubber.

Figure 3:
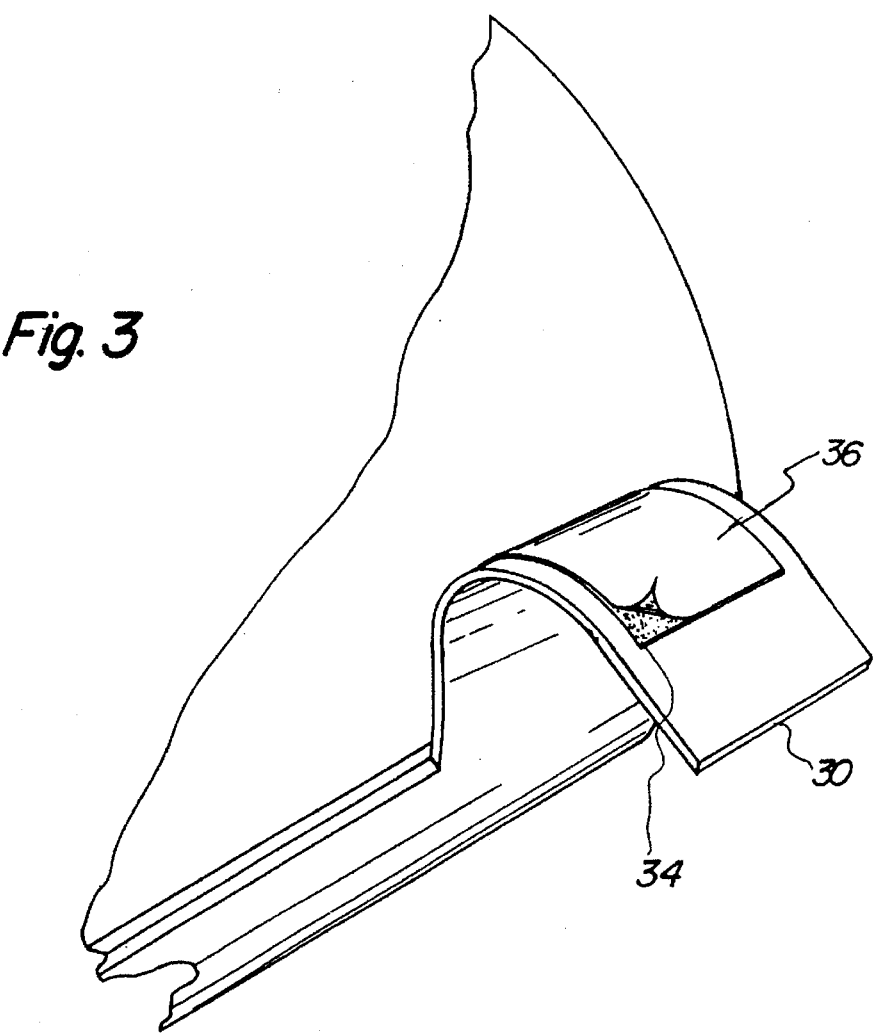
FIG. 3 is a cut-away sectional view of the tab at position 3 of the present invention of FIG. 1.

An adhesive 34 is provided on the radially interior face of each tab 30, as shown in FIG. 3. The adhesive is for contacting the minor circumferential extent, and to allow the proximal end of the tube to be securely positioned at the base of the penis. The adhesive prevents the tube, when positioned around the penis, from sliding off the penis. The adhesive has a layer of protective covering 36 thereon. The protective covering is pulled back and off the adhesive prior to positioning of each tab on the minor circumferential extent. Each tab 30, as shown in FIG. 1, is spaced apart from another tab when the adhesive causes each tab to be secured at the base of the penis. The adhesive allows the tabs, when position at the base of the penis, to constrict the diameter of the proximal end about 30 to 50 percent.

Additionally, a layer of liquid absorbing hydrophillic material 38 is secured to the entire interior of the tube.

Figure 4:
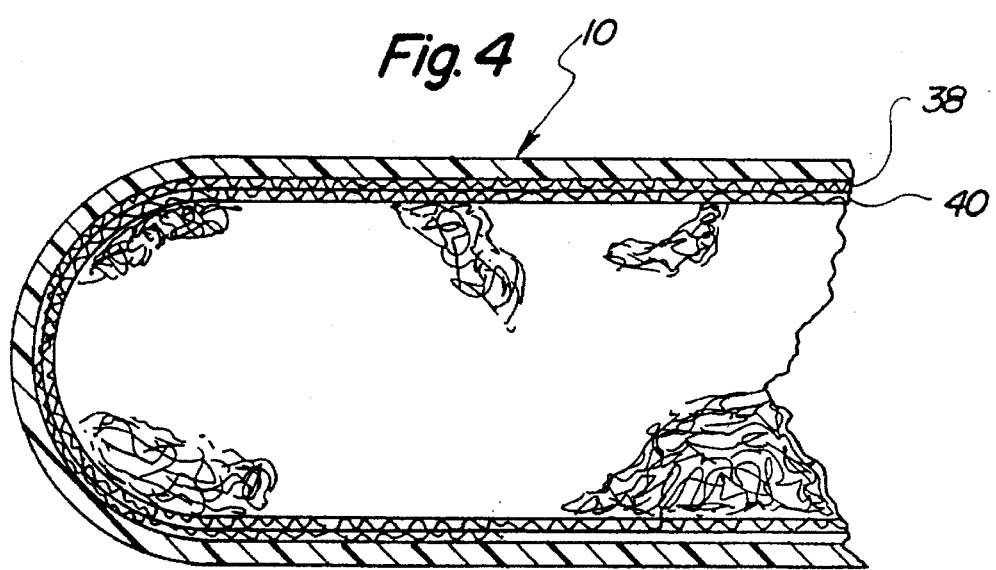
FIG. 4 is a sectional view of the present invention of FIG. 1 taken along line 4—4 of FIG. 1.

FIG. 4 depicts the layer as shown by a sectional view of FIG. 1.

Lastly, a layer of dry weave hydrophobic material 40 is provided. The hydrophobic material is secured throughout the layer of hydrophilic material over its entire extent and positionable in contact with the penis of a wearer. The hydrophilic layer and the hydrophobic layer when combined allow the tube to be positioned over the penis. The tube is able to abate the problem of dribbling. The wearer may wear the device under his trousers knowing the device is not visible to others.

The present invention provides an easy to use tubular device for the penis of an incontinent male. The device absorbs moisture from dribbling while allowing the user to feel dry. The soft thin flexible rubber exterior allows freedom of movement and prevents irritation to the scrotum and inner thigh. The slits allow the device to fit snugly around the penis at the base. The present invention gives the wearer a sense of confidence when in public.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the United States is as follows:

1. A tubular device for the penis of an incontinent male comprising in combination:

- a tube having a closed hemispherical distal end and an open generally circular proximal end, the tube having a length being between about 6 to 7½ inches, the tube having a central axis when in use with an imperforate cylindrical wall of a diameter from about 2 inches to 2½ inches, the hemispherical distal end and the cylindrical wall constituting about seventy-five percent of the length of the tube;

- a pair of axial slits extending from the proximal end, the slits having a length of about from ⅓ inch to ¼ inch from the proximal end for a distance of about twenty five percent of the length of the tube, the slits thereby dividing the proximal end into a major circumferential extent and a minor circumferential extent extending axially from the distal end at an equal distance;

- a pair of lateral tabs extending from the major circumferential extent from adjacent to each slit to overlap different regions of the minor circumferential extent of the tube thereadjacent, each tab having a width of about ½ inch and a length being 1 inch from the major circumferential extent, each tab and the tube being integrally formed of a soft thin flexible rubber;

- adhesive on the radially interior face of each tab for contacting the minor circumferential extent to allow the proximal end of the tube to be securely positioned at the base of the penis, the adhesive having a layer of protective covering thereon, the protective covering capable of being pulled back and off the adhesive prior to each tab being positioned on the minor circumferential extent, each tab being spaced apart from another tab when the adhesive causing each tab to be secured at the base, the adhesive allowing the tabs when positioned at the base to constrict the diameter of the proximal end about 30 to 50 percent;

- a layer of liquid absorbing hydrophilic material secured to the entire interior of the tube; and

- a layer of dry weave hydrophobic material secured throughout the layer of hydrophilic material over its entire extent and positionable in contact with the penis of the wearer.

* * * * *